(12) United States Patent
Franklin

(10) Patent No.: US 10,569,062 B2
(45) Date of Patent: Feb. 25, 2020

(54) LOW PROFILE OCCLUSION CATHETER

(71) Applicant: Prytime Medical Devices, Inc., Boerne, TX (US)

(72) Inventor: Curtis J. Franklin, Lakewood, CO (US)

(73) Assignee: Prytime Medical Devices, Inc., Boerne, TX (US)

( * ) Notice: Subject to any disclaimer, the term of this patent is extended or adjusted under 35 U.S.C. 154(b) by 62 days.

(21) Appl. No.: 14/917,286

(22) PCT Filed: Sep. 9, 2014

(86) PCT No.: PCT/US2014/054802
§ 371 (c)(1),
(2) Date: Mar. 8, 2016

(87) PCT Pub. No.: WO2015/035393
PCT Pub. Date: Mar. 12, 2015

(65) Prior Publication Data
US 2016/0213893 A1    Jul. 28, 2016

Related U.S. Application Data

(60) Provisional application No. 62/010,275, filed on Jun. 10, 2014, provisional application No. 61/875,498, filed on Sep. 9, 2013.

(51) Int. Cl.
*A61M 25/10* (2013.01)
*A61L 29/02* (2006.01)
(Continued)

(52) U.S. Cl.
CPC ......... *A61M 25/1006* (2013.01); *A61L 29/02* (2013.01); *A61L 29/04* (2013.01);
(Continued)

(58) Field of Classification Search
CPC ........ A61M 25/008; A61M 2025/0081; A61M 2025/0002; A61M 25/1006;
(Continued)

(56) References Cited

U.S. PATENT DOCUMENTS 2,156,289 A    5/1939  Hoy
4,464,172 A    8/1984  Lichtenstein
(Continued)

FOREIGN PATENT DOCUMENTS

EP    1094861 B1    4/2005
EP    1658808 A1    5/2006
(Continued)

OTHER PUBLICATIONS

Extended European Search Report dated Jun. 26, 2017 in EP Application No. 14842370.
(Continued)

*Primary Examiner* — Kathleen S Holwerda
*Assistant Examiner* — Brooke Labranche
(74) *Attorney, Agent, or Firm* — Panitch Schwarze Belisario & Nadel LLP

(57) ABSTRACT

A low profile occlusion catheter having a guiding atraumatic tip that prevents entry of the balloon into collateral vessels. The occlusion catheter system is particularly well suited for use in vascular occlusion and includes a pressure monitoring line to monitor the degree and state of occlusion.

20 Claims, 9 Drawing Sheets

(51) Int. Cl.
*A61L 29/06* (2006.01)
*A61L 29/18* (2006.01)
*A61M 25/00* (2006.01)
*A61L 29/04* (2006.01)

(52) U.S. Cl.
CPC .............. *A61L 29/06* (2013.01); *A61L 29/18* (2013.01); *A61M 25/008* (2013.01); *A61M 25/0068* (2013.01); *A61L 2400/16* (2013.01); *A61M 2025/0002* (2013.01); *A61M 2025/1079* (2013.01)

(58) Field of Classification Search
CPC ................ A61M 2025/1079; A61L 29/06; A61L 29/02; A61L 29/04; A61L 29/18; A61L 2400/16; C08L 77/12
See application file for complete search history.

(56) References Cited

U.S. PATENT DOCUMENTS

| | | |
|---|---|---|
| 4,713,888 A | 12/1987 | Broselow |
| 4,777,951 A | 10/1988 | Cribier et al. |
| 4,823,469 A | 4/1989 | Broselow |
| 4,865,549 A | 9/1989 | Sonsteby |
| 4,926,885 A | 5/1990 | Hinkle |
| 4,983,166 A | 1/1991 | Yamawaki |
| 5,047,045 A * | 9/1991 | Arney ................ A61M 25/104 604/103.1 |
| 5,135,494 A | 8/1992 | Engelson et al. |
| 5,169,386 A * | 12/1992 | Becker .................... A61F 2/04 600/435 |
| 5,282,479 A | 2/1994 | Havran |
| 5,320,605 A | 6/1994 | Sahota |
| 5,383,856 A | 1/1995 | Bersin |
| 5,447,503 A | 9/1995 | Miller |
| 5,505,702 A | 4/1996 | Arney |
| 5,522,400 A | 6/1996 | Williams |
| 5,571,093 A | 11/1996 | Cruz et al. |
| 5,718,678 A | 2/1998 | Fleming, III |
| 5,738,652 A | 4/1998 | Boyd et al. |
| 5,911,702 A | 6/1999 | Romley et al. |
| 6,011,988 A | 1/2000 | Lynch et al. |
| 6,013,019 A | 1/2000 | Fischell et al. |
| 6,102,930 A | 8/2000 | Simmons, Jr. |
| 6,113,579 A * | 9/2000 | Eidenschink ..... A61M 25/0068 604/264 |
| 6,146,370 A | 11/2000 | Barbut |
| 6,161,547 A | 12/2000 | Barbut |
| 6,165,199 A | 12/2000 | Barbut |
| 6,190,356 B1 | 2/2001 | Bersin |
| 6,231,572 B1 | 5/2001 | Hart et al. |
| 6,248,121 B1 | 6/2001 | Nobles |
| 6,280,434 B1 | 8/2001 | Kinoshita et al. |
| 6,423,031 B1 | 7/2002 | Donlon |
| 6,453,572 B2 | 9/2002 | Cross et al. |
| 6,575,932 B1 | 6/2003 | O'Brien et al. |
| 6,579,221 B1 | 6/2003 | Peterson |
| 6,602,270 B2 | 8/2003 | Leschinsky et al. |
| 6,656,153 B1 | 12/2003 | Sakai et al. |
| 6,666,814 B2 | 12/2003 | Downey et al. |
| 6,669,679 B1 | 12/2003 | Savage et al. |
| 6,679,860 B2 | 1/2004 | Stiger |
| 6,695,811 B2 | 2/2004 | Samson et al. |
| 6,719,270 B2 | 4/2004 | Ozawa |
| 6,719,720 B1 | 4/2004 | Voelker et al. |
| 6,733,513 B2 | 5/2004 | Boyle et al. |
| 6,735,532 B2 | 5/2004 | Freed et al. |
| 6,736,790 B2 | 5/2004 | Barbut et al. |
| 6,746,462 B1 | 6/2004 | Selmon et al. |
| 6,796,959 B2 | 9/2004 | Davis et al. |
| 6,936,056 B2 | 8/2005 | Nash et al. |
| 6,979,318 B1 | 12/2005 | McDonald et al. |
| 7,341,571 B1 | 3/2008 | Harris et al. |
| 7,434,326 B2 | 10/2008 | Gifford |
| 7,503,904 B2 | 3/2009 | Choi |
| 7,503,909 B2 | 3/2009 | Kusu et al. |
| 7,763,043 B2 | 7/2010 | Goodin et al. |
| 7,892,469 B2 | 2/2011 | Lim et al. |
| 7,909,810 B2 | 3/2011 | Noone |
| 7,951,186 B2 | 5/2011 | Eidenschink et al. |
| 7,951,819 B2 | 5/2011 | Niculescu-Duvaz et al. |
| 7,959,644 B2 | 6/2011 | Shriver |
| 8,088,103 B2 | 1/2012 | Teeslink et al. |
| 8,162,879 B2 | 4/2012 | Hattangadi et al. |
| 8,241,241 B2 | 8/2012 | Evans et al. |
| 8,262,611 B2 | 9/2012 | Teeslink et al. |
| 8,419,648 B2 * | 4/2013 | Corl ..................... A61B 5/0215 600/485 |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,655,798 B2 | 2/2014 | Humphrey et al. |
| 8,672,868 B2 | 3/2014 | Simons |
| 8,747,358 B2 | 6/2014 | Trombley, III et al. |
| 8,814,900 B2 | 8/2014 | Fleming, III |
| 8,900,214 B2 | 12/2014 | Nance et al. |
| 8,948,848 B2 | 2/2015 | Merhi |
| 8,951,565 B2 | 2/2015 | McCarthy |
| 9,131,874 B2 | 9/2015 | Eliason et al. |
| D748,257 S | 1/2016 | Franklin |
| 9,414,843 B2 | 8/2016 | Pavcnik et al. |
| 9,474,882 B2 | 10/2016 | Franklin |
| 9,687,333 B2 * | 6/2017 | Angel ............... A61M 25/0029 |
| 2002/0193735 A1 | 12/2002 | Stiger |
| 2003/0032974 A1 | 2/2003 | Leschinsky et al. |
| 2003/0167038 A1 | 9/2003 | Yozu et al. |
| 2004/0073162 A1 | 4/2004 | Bleam et al. |
| 2004/0082935 A1 * | 4/2004 | Lee .................... A61M 25/0029 604/523 |
| 2004/0254528 A1 | 12/2004 | Adams et al. |
| 2005/0059931 A1 | 3/2005 | Garrison et al. |
| 2005/0148812 A1 | 7/2005 | Nigroni et al. |
| 2005/0261725 A1 | 11/2005 | Crawford et al. |
| 2007/0043307 A1 | 2/2007 | Raulerson et al. |
| 2007/0043409 A1 | 2/2007 | Brian et al. |
| 2007/0129466 A1 | 6/2007 | Kagawa et al. |
| 2007/0135830 A1 * | 6/2007 | Schaeffer .......... A61M 25/0068 606/192 |
| 2007/0219466 A1 | 9/2007 | Tremulis et al. |
| 2007/0219488 A1 | 9/2007 | Francescatti |
| 2008/0027356 A1 | 1/2008 | Chen et al. |
| 2008/0082046 A1 | 4/2008 | Kato et al. |
| 2008/0082119 A1 | 4/2008 | Vitullo |
| 2008/0243067 A1 | 10/2008 | Rottenberg et al. |
| 2008/0262477 A1 | 10/2008 | Djaladat |
| 2009/0026595 A1 | 1/2009 | Kadoi |
| 2009/0062666 A1 | 3/2009 | Roteliuk |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 * | 12/2009 | Boudreault .......... A61B 17/025 606/86 R |
| 2010/0016735 A1 | 1/2010 | Harpas et al. |
| 2010/0041984 A1 | 2/2010 | Shapland et al. |
| 2010/0234915 A1 | 9/2010 | Herlich et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2011/0196412 A1 | 8/2011 | Levit et al. |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 * | 5/2012 | Turovskiy ............... A61B 18/02 606/21 |
| 2012/0172911 A1 | 7/2012 | Welch |
| 2012/0215166 A1 | 8/2012 | Barki |
| 2012/0271231 A1 | 10/2012 | Agrawal |
| 2012/0302994 A1 | 11/2012 | Wilson et al. |

(56) References Cited

U.S. PATENT DOCUMENTS

| | | |
|---|---|---|
| 2013/0102926 A1 | 4/2013 | Eliason et al. |
| 2013/0102929 A1 | 4/2013 | Haight et al. |
| 2013/0190619 A1 | 7/2013 | Nudel |
| 2013/0281869 A1 | 10/2013 | Barbut et al. |
| 2013/0289607 A1 | 10/2013 | Pedersen et al. |
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0316012 A1 | 10/2014 | Freyman et al. |
| 2014/0378869 A1 | 12/2014 | Sela et al. |
| 2015/0012031 A1 | 1/2015 | Rago et al. |
| 2015/0039012 A1 | 2/2015 | Solar et al. |
| 2015/0367098 A1 | 12/2015 | Aggerholm et al. |
| 2016/0000446 A1 | 1/2016 | Eliason et al. |

FOREIGN PATENT DOCUMENTS

| | | |
|---|---|---|
| EP | 1911484 A2 | 4/2008 |
| EP | 2389974 A1 | 11/2011 |
| EP | 2716323 A1 | 4/2014 |
| GB | 2297259 A | 7/1996 |
| JP | H 03198868 A | 8/1991 |
| JP | H 09-164208 A | 6/1997 |
| JP | 2000217922 A | 8/2000 |
| JP | 2002505165 A | 2/2002 |
| JP | 2003535652 A | 12/2003 |
| JP | 200714820 A | 1/2007 |
| JP | 2008546471 A | 12/2008 |
| JP | 2011245300 A | 12/2011 |
| WO | 9220398 A1 | 11/1992 |
| WO | 9713542 A1 | 4/1997 |
| WO | 9834670 A2 | 8/1998 |
| WO | 1999/24105 A2 | 5/1999 |
| WO | 9944666 A2 | 9/1999 |
| WO | 0197743 A2 | 12/2001 |
| WO | 2004049970 A2 | 6/2004 |
| WO | 2006135853 A2 | 12/2006 |
| WO | 2007001701 A1 | 1/2007 |
| WO | 2007022592 A1 | 3/2007 |
| WO | 2008013441 A1 | 1/2008 |
| WO | 2010070685 A1 | 6/2010 |
| WO | 2011133736 A2 | 10/2011 |
| WO | 2014/003809 A1 | 1/2014 |
| WO | 2014134215 A1 | 9/2014 |
| WO | 2014152191 A1 | 9/2014 |
| WO | 2015/006828 A1 | 1/2015 |
| WO | 2015035393 A1 | 3/2015 |
| WO | 2015191685 A1 | 12/2015 |
| WO | 2016149653 A2 | 9/2016 |

OTHER PUBLICATIONS

Int'l Preliminary Report dated Jul. 17, 2017 in Int'l Application No. PCT/US2016/023223.
Int'l Search Report and Written Opinioin dated Sep. 28, 2017 in Int'l Application No. PCT/US2017/035729.
Office Action dated Sep. 19, 2017 in JP Application No. 2015-559309.
Office Action dated Sep. 12, 2017 in JP Application No. 2016-546035.
Office Action dated Oct. 12, 2017 in CA Application No. 2,980,018.
Extended Search Report dated Mar. 24, 2017 in EP Application No. 14842370.
Int'l Search Report and Written Opinion dated Apr. 21, 2017 in Int'l Application No. PCT/US2016/023223.
Extended Search Report dated Mar. 21, 2017 in EP Application No. 15806534.
Office Action dated Apr. 11, 2017 in JP Application No. 2016-546035.
Office Action dated Mar. 20, 2017 in CA Application No. 2,797,237.
Extended European Search Report dated Oct. 5, 2016 in Europe Application No. EP 14 75 6640.
Supplemental Search Report dated Dec. 19, 2016 in EP Application No. 15806534.
Int'l Preliminary Report dated Dec. 22, 2016 in Int'l Application No. PCT/US2015/035061.
Int'l Search Report and Written Opinion dated Sep. 4, 2015 in Int'l Application No. PCT/US2014/035061.
Office Action dated Aug. 23, 2016 in AU Application No. 2015274743.
Holcomb et al., "Causes of death in US Special Operations Forces in the global war on terrorism: 2001-2004," Annals of Surgery, vol. 245, No. 6, pp. 986-991 (2007).
Sohn et al., "Demographics, Treatment, and Early Outcomes in Penetrating Vascular Combat Trauma," Arch Surg, vol. 143, No. 8, pp. 783-787 (2008).
White et al., "The Epidemiology of Vascular Injury in the Wars in Iraq and Afghanistan," Annals of Surgery, vol. 253, No. 6, pp. 1184-1189.
Fenton et al., "Comparing risks of alternative medical diagnosis using Bayesian arguments," J. Biomed. Inf., vol. 43, pp. 485-495 (2010).
Patel et al., "Bayesian Designs for Device Clinical Trials," MDG Forum, Waltham, MA., Nov. 3, 2010, downloaded from web page: <http://www.cytel.com/pdfs/Patel_Bayes_Devices_Slides_11.18.10.pdf>.
Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.
Int'l Preliminary Report on Patentability dated Sep. 1, 2015 in Int'l Application No. PCT/US2014/018779.
Int'l Search Report and Written Opinion dated Jun. 8, 2014 in Int'l Application No. PCT/US2014/018779.
Int'l Search Report and Written Opinion dated Oct. 14, 2011 in Int'l Application No. PCT/US2011/033368.
Sandgren et al., "The Diameter of the Common Femoral Artery in Healthy Human: Influence of Sex, Age, and Body Size," Journal of Vascular Surgery, vol. 29, No. 3, pp. 503-510 (1999).
Sam II et al., "Blunt Traumatic Aortic Transection: Endoluminal Repair with Commercially Available Aortic Cuffs," Journal of Vascular Surgery, vol. 38, No. 5, pp. 1132-1135 (2003).
Peterson et al., "Percutaneous endovascular repair of blunt thoracic aortic transection," Journal of Trauma, vol. 59, No. 5, pp. 1062-1065 (2005).
Office Action dated Oct. 28, 2014 in U.S. Appl. No. 13/642,465.
Office Action dated Apr. 6, 2015 in U.S. Appl. No. 13/642,465.
Stannard et al., "Resuscitative Endovascular Balloon Occlusion of the Aorta (REBOA) as an Adjunct for Hemorrhagic Shock," J. Trauma, vol. 71, pp. 1869-1872 (2011).
Ledgerwood et al., "The Role of Thoracic Aortic Occlusion for Massive Hemoperitoneum," J Trauma, vol. 16, No. 8, pp. 610-615 (1976).
Detrano et al. "Bayesian Probability Analysis: a Prospective Demonstration of its Clinical Utility in Diagnosing Coronary Disease," Circulation, vol. 69, No. 3, pp. 541-547 (1984).
Int'l Search Report and Written Opinion dated Jan. 28, 2015 in Int'l Application No. PCT/US2014/054802.
Int'l Preliminary Report on Patentability dated Mar. 24, 2016 in Int'l Application No. PCT/US2014/054802.
Int'l Preliminary Report on Patentability dated Nov. 1, 2012 in Int'l Application No. PCT/US2011/033368.
Langewouters et al., "The static elastic properties of 45 human thoracic and 20 abdominal aortas in vitra and the parameters of a new model," Journal of Biometrics, vol. 17, No. 6, pp. 425-435 (1984).
Hughes, "Use of an Intra-Aortic Balloon Catheter Tamponade for Controlling Intra-Abdominal Hemorrhage in Man," Surgery, vol. 36, pp. 65-68 (1954).
Chen et al., "The Renal Length Nomogram: A Multivariable Approach," The Journal of Urology, vol. 168, pp. 2149-2152 (Nov. 2002).

\* cited by examiner

LOW PROFILE OCCLUSION CATHETER

CROSS-REFERENCE TO RELATED APPLICATIONS

The present application is a national stage application under 35 U.S.C. § 371 of International Patent Application No. PCT/US2014/054802, filed Sep. 9, 2014 and titled, "Low-Profile Balloon Occlusion Catheter," which was published under International Publication No. WO 2015/035393 A1 and claims the benefit of U.S. Provisional Patent Application Nos. 62/010,275, filed on Jun. 10, 2014 and 61/875,498, filed Sep. 9, 2013, both titled, "Low-Profile Balloon Catheter," each of the disclosures of which are incorporated herein by reference.

STATEMENT REGARDING FEDERALLY SPONSORED RESEARCH OR DEVELOPMENT

This invention was made with government support under Contract No. W81XWH-12-1-0558 awarded by U.S. Army Medical Research Materiel Command. The government has certain rights in the invention.

BACKGROUND

The invention generally relates to percutaneously introduced occlusion catheters, and more particularly to an occlusion catheter having an atraumatic guiding tip formed of an elastomeric polymer. More particularly, the present invention pertains to an occlusion catheter in which the atraumatic guiding tip is formed of entirely of polymer, polymer reinforced with a shape memory or superelastic material, or entirely of a shape memory or superelastic material. Still more particularly, the present invention pertaint to an occlusion cathter having at least one lumen suitably configured to introduce or withdraw body fluids from a patient into which the cathter is placed, and/or for sensing a condition within the body, such as, for example, pressure or flow rate in the region of the catheter. Yet still more particularly, the present invention pertains to an occlusion catheter having a first catheter member with a first lumen extending longitudinally through the first catheter member and open at a distal end of the first catheter member; a second catheter member having a second lumen extending longitudinally through the second catheter member and open at a distal end of the second catheter member, the second catheter member is positioned over and in spaced apart relationship relative to a proximal section of the first catheter member forming an annular space between the second catheter member and the first catheter member, the proximal section of the first catheter member resides within the second lumen of the second catheter member and the first catheter member extends beyond the distal end of the second catheter member, a third catheter member having a third lumen extending longitudinally through the third catheter member and open at a distal end of the third catheter member; the third catheter member is positioned over a distal section of the first catheter member, the third catheter member having a distal section that extends distally from a distal end of the first catheter member such that the first lumen and the third lumen are in fluid flow communication, whereby the second and third catheter are spaced apart from each other along a longitudinal axis of the first catheter member with the first catheter member extending there between; the atraumatic guiding tip member being joined to a distal end of the third catheter member; and an expandable member, such as a balloon, coupled to the second catheter member and to the third catheter member, such that the space between the second catheter member and the third catheter member is within an area bounded by the expandable member.

Balloon catheters generally comprise an elongated catheter shaft with an expandable balloon on the distal end of the shaft, and are used in a number of different medical procedures, including, for example, angioplasty, stent placement, occlusion, drug deliver, etc. The catheter is introduced through a percutaneous introducer sheath and maneuvered into the patient's blood vessels until the balloon is properly positioned within the body, such as at the stenotic site to be dilated or at a site requiring occlusion, drug delivery or other procedure such as stent placement.

It is often desirable for balloon catheters to have very low profiles in order to facilitate passage of the balloon across severe and remote vascular obstructions. High strength materials are commonly required in the design of balloon catheter components to prevent shaft buckling when the balloon is inflated. Additionally, high strength materials are required so that torque applied to the proximal end of the catheter results in rotation of the distal tip of the catheter. High flexibility materials are also commonly required in the design of balloon catheter components to maintain a low-profile and avoid trauma or perforation of the blood vessels while the catheter is maneuvered through the patient's tortuous vasculature.

Conventional balloon catheters, particularly those intended for vascular occlusion, do not adequately balance the need for proximal segment stiffness with the need for low profile, flexible distal segment and trackability through the tortious vascular pathway without entry into collateral vessels. Therefore, a need exists for a low profile occlusion catheter with a high strength and relatively stiff proximal segment and a flexible distal segment with an atraumatic tip having a design that permits tracking along the major vessels while preventing entry into collateral vessels.

SUMMARY OF THE INVENTION

Described herein are systems, methods and compositions for an occlusion catheter system comprising: a first catheter member having a first lumen extending longitudinally through the first catheter member and open at a distal end of the first catheter member; a second catheter member having a second lumen extending longitudinally through the second catheter member and open at a distal end of the second catheter member, the second catheter member is positioned over and in spaced apart relationship relative to a proximal section of the first catheter member forming an annular space between the second catheter member and the first catheter member, the proximal section of the first catheter member resides within the second lumen of the second catheter member and the first catheter member extends beyond the distal end of the second catheter member, a third catheter member having a third lumen extending longitudinally through the third catheter member and open at a distal end of the third catheter member; the third catheter member is positioned over a distal section of the first catheter member, the third catheter member having a distal section that extends distally from a distal end of the first catheter member such that the first lumen and the third lumen are in fluid flow communication, whereby the second and third catheter are spaced apart from each other along a longitudinal axis of the first catheter member with the first catheter member extending there between; an atraumatic tip member having a proximal section co-axially coupled to a distal end of the third catheter member and terminating the third lumen in the third catheter member; and an expandable occlusion member, such as a balloon, coupled at its proximal end to the second catheter member and at its distal end to the third catheter member and in fluid flow communication with the second lumen of the second catheter member, the expandable occlusion member being positioned such that the longitudinal space between the second catheter member and the third catheter member is within the expandable occlusion member.

Also disclosed herein are systems, methods and compositions for occlusion catheter system comprising: a first catheter member having a first and second lumens extending along a longitudinal axis thereof that forms a proximal section of the catheter system, a second catheter member having a third lumen forming a distal section of the catheter system and coupled to a distal end of the first catheter member, an expandable occlusion balloon coupled at its proximal end to a distal end of the first catheter member and at its distal end to a proximal end of the second catheter member, a first lumen of the first catheter member terminating within the expandable occlusion balloon to communicate an inflation fluid to an area within the expandable occlusion balloon and a second lumen of the first catheter member being in fluid flow communication with the third lumen of the second catheter member, an atraumatic guiding tip coupled to a distal end of the third lumen of the second catheter member; and a third catheter member having at least one lumen passing longitudinally there through, the third catheter member being disposed within each of the second lumen of the first catheter member and the third lumen of the second catheter member and passing there through.

The methods, systems, and apparatuses are set forth in part in the description which follows, and in part will be apparent from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1:
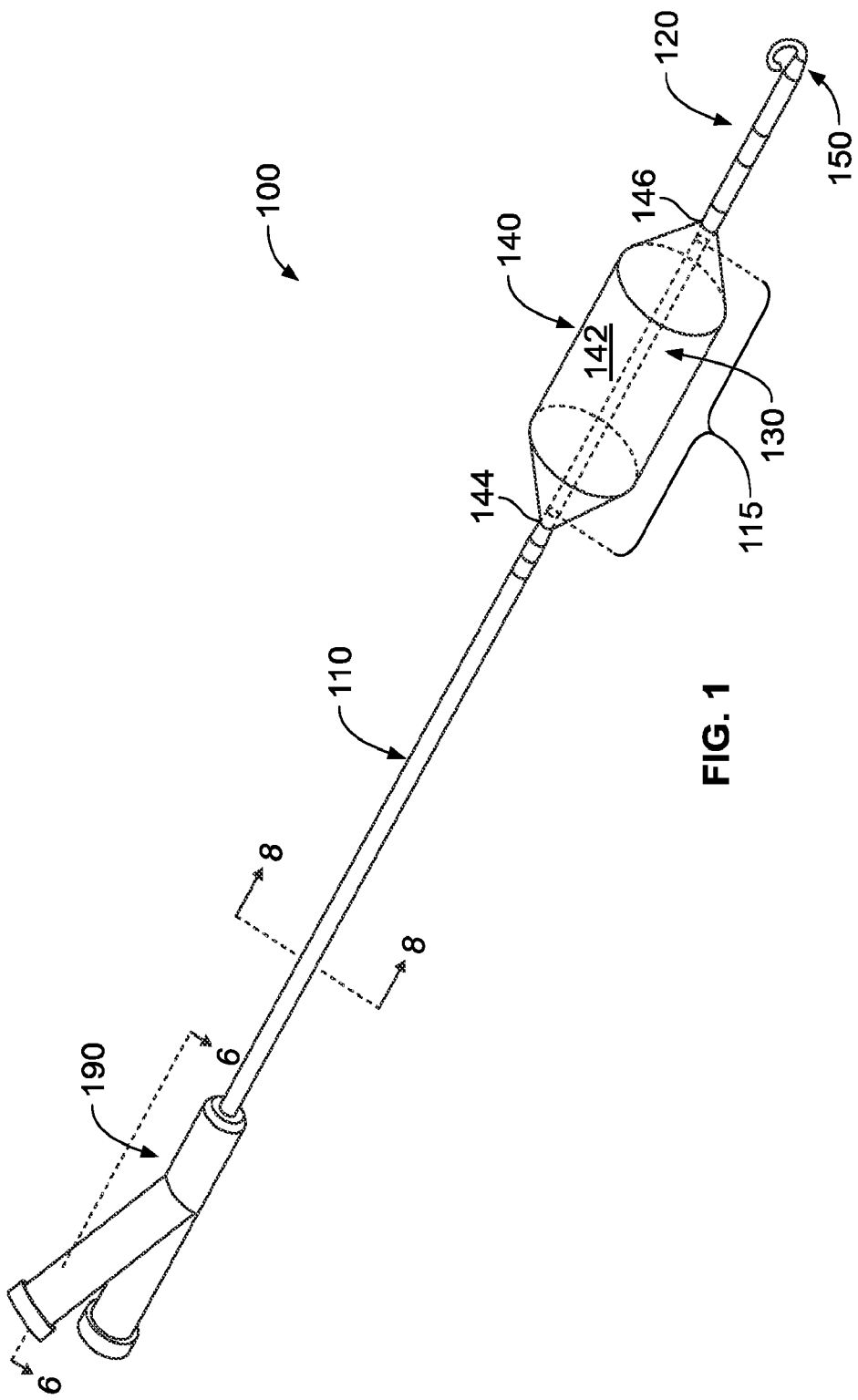
FIG. 1 is a perspective view of an embodiment of a occlusion catheter described herein.
Figure 2:
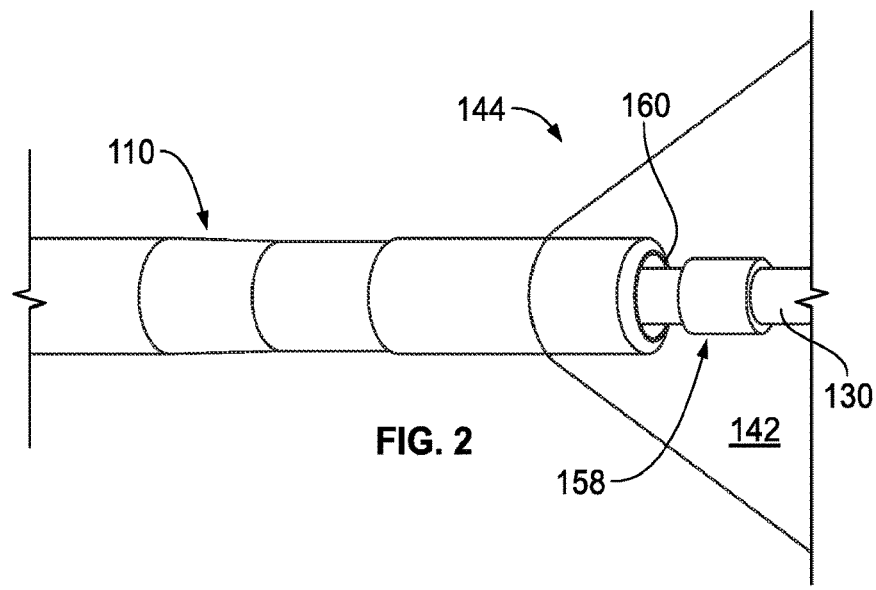
FIG. 2 is an enlarged perspective view of the first port of the inventive occlusion catheter depicted in FIG. 1.
Figure 3:
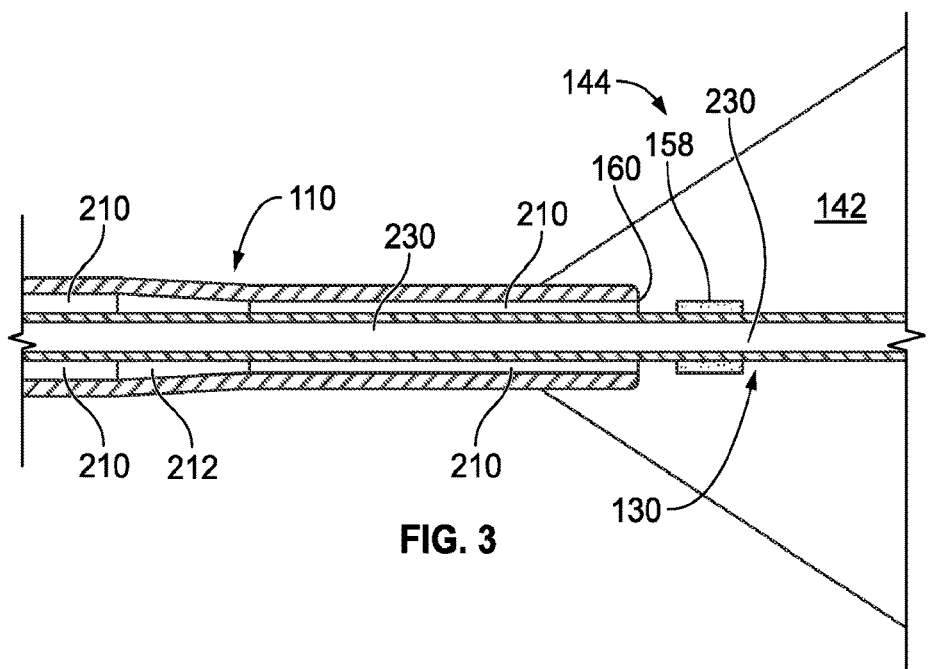
FIG. 3 is a longitudinal cross-sectional view of FIG. 2.

The foregoing and other features and advantages of the invention will become more apparent from the following detailed description of exemplary embodiments, read in conjunction with the accompanying drawings. The detailed description and drawings are merely illustrative of the invention rather than limiting, the scope of the invention being defined by the appended claims and equivalents thereof.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

Furthermore, while the invention is described as an occlusion catheter system, it will be understood that the inventive occlusion catheter system may be used clinically for a variety of different therapeutic or diagnostic indications involving vascular interventions, including, for example and without limitation, vascular occlusion, angioplasty, stent delivery, artherectomy, drug delivery, imaging or the like. In accordance with an exemplary and preferred embodiment, the inventive occlusion catheter system is well suited for use as a vascular occlusion catheter, and in particular an aortic occlusion balloon catheter. Applications making advantageous use of embodiments of the invention may use any suitable access site for vascular intervention. For example, applications of the catheter system may involve access at the femoral artery, the brachial artery, the subclavian artery, or any other blood vessel suitable for use as an access site for catheterization, including venous vessels.

In the following description, when reference is made to the terms "proximal" or "proximally" it is intended to mean a portion or component of the inventive occlusion catheter system that is oriented away from the body into which the system is or is intended to be placed. Conversely, when reference is made to the terms "distal" or "distally" it is intended to mean a portion or component of the inventive occlusion catheter system that is oriented toward the body into which the system is or is intended to be placed. Thus, for example, the guiding atraumatic tip described hereinafter is located at a distal end of the occlusion catheter system, while the proximal hub is located at a proximal end of the occlusion catheter system.

As shown in the accompanying Figures, the occlusion catheter system 100 generally includes a catheter assembly having a first catheter member 130 having a first lumen 230, a second catheter member 110 having a second lumen 210, a third catheter member 120 having a third lumen 220, an expandable occlusion member 140, a proximal hub 190 and a guiding atraumatic tip 150. The first lumen 230 of the first catheter member 130 extends longitudinally through the first catheter member and is coupled at its proximal end to the proximal hub 190 and at its distal end to a proximal section of the third catheter member 120 and in fluid flow communication with the third lumen 220 of the third catheter member 120. The second lumen 210 of the second catheter member 110 also extends longitudinally through the second catheter member 110, and terminates in a first port 160 distal to a proximal end of and within a space 142 defined by the expandable occlusion balloon 140, such that the second lumen 210 is in fluid flow communication with the space 142 within the expandable occlusion member 140 to convey a fluid to and from the expandable occlusion member 140 from a fluid source external the occlusion catheter system 100, coupled to the proximal hub 190 via extension lines (not shown) and in fluid communication with the second lumen 210. The third catheter member 120 is coupled at a proximal end thereof to a distal end of the first catheter member 130 such that the third lumen 220 of the third catheter member 120 is in fluid flow communication with the first lumen 230 of the first catheter member 130. The second catheter member 110 and the third catheter member 120 are positioned in longitudinal co-axial spaced apart relationship from one and other along a longitudinal axis of the first catheter member 130 thereby defining an intermediate region 115 of the first catheter member 130 within the space 142 within the expandable occlusion balloon 140 that is not covered by either the second catheter member 110 or the third catheter member 120.

The expandable member, such as an expandable occlusion balloon, 140 is attached, at its proximal end 144 to a distal end of the second catheter member 110 and at its distal end 146 to a proximal end of the third catheter member 120. Referring to FIGS. 2-5, a proximal radio opaque marker 158 may be affixed to the first catheter member 130 at or near the first port 160, which is near the attachment position of the expandable occlusion balloon at the proximal end 144 of the expandable occlusion balloon 140. A distal radio opaque marker 159 may be affixed to the first catheter member 130 near the attachment position of the expandable occlusion balloon on the distal end 146 of the expandable occlusion balloon 140. The proximal and distal radio opaque markers 158, 159 may be implemented as bands made of a radio opaque material. In one example, the radio opaque material is a metal that is radio opaque such as stainless steel, or an alloy, such as a platinum iridium alloy. In another example, the proximal and distal radio opaque markers 158, 159 may be sections of the catheters that have been impregnated with radio opaque material such as for example stainless steel or a suitable alloy. In another example, the proximal and distal radio opaque markers 158, 159 may be implemented as bands or sections of polymer, such as, for example, polyether block amide copolymer (PEBAX, Arkema, Paris, France) that has been mixed or doped with a radio opaque substance, such as, for example, barium sulfate. The implementation of the proximal and distal radio opaque markers 158, 159 on the catheter system would aid in visualization of the balloon position within the vasculature using fluoroscopy or x-ray.

When an expandable occlusion balloon 140 is employed, it is inflated by introducing an inflation fluid, such as saline, from an external source, such as a syringe, coupled to the proximal hub 190, into and through the second lumen 210, out of the first port 160 and into the space 142 within the expandable occlusion balloon 140. As is known in the art, the inflation fluid is introduced until the expandable occlusion balloon 140 is inflated to a desired diameter volume, pressure or visual appearance when visualized using imaging modalities such as X-ray or fluoroscopy. Deflation of the expandable occlusion balloon 140 is simply the reverse process of withdrawing the inflation fluid from the space 142 of the inflation balloon 140. In its deflated or collapsed state, the inflation balloon 140 will be positioned either within or adjacent to the intermediate region 115 of the first catheter member 130, thereby providing a lower profile to the entire occlusion catheter system 100.

Figure 4:
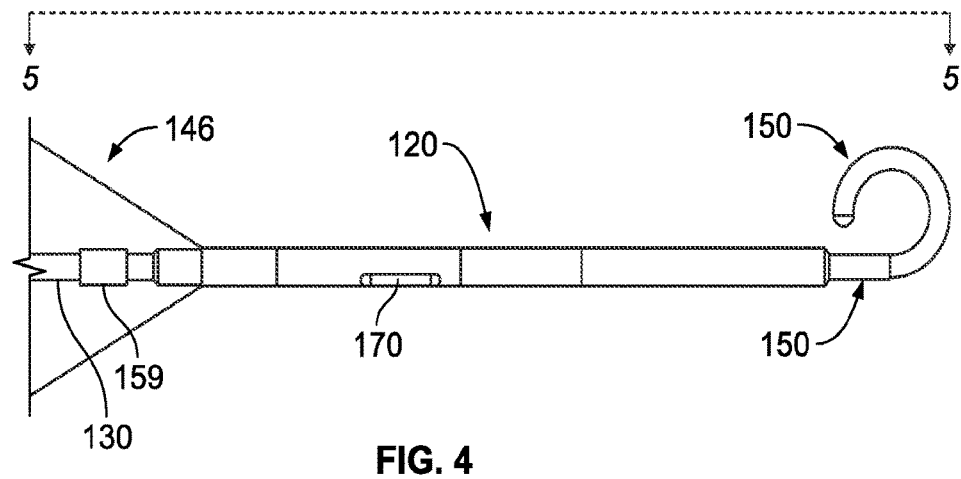
FIG. 4 is a perspective view of a distal section of the inventive occlusion catheter depicted in FIG. 1
Figure 5:
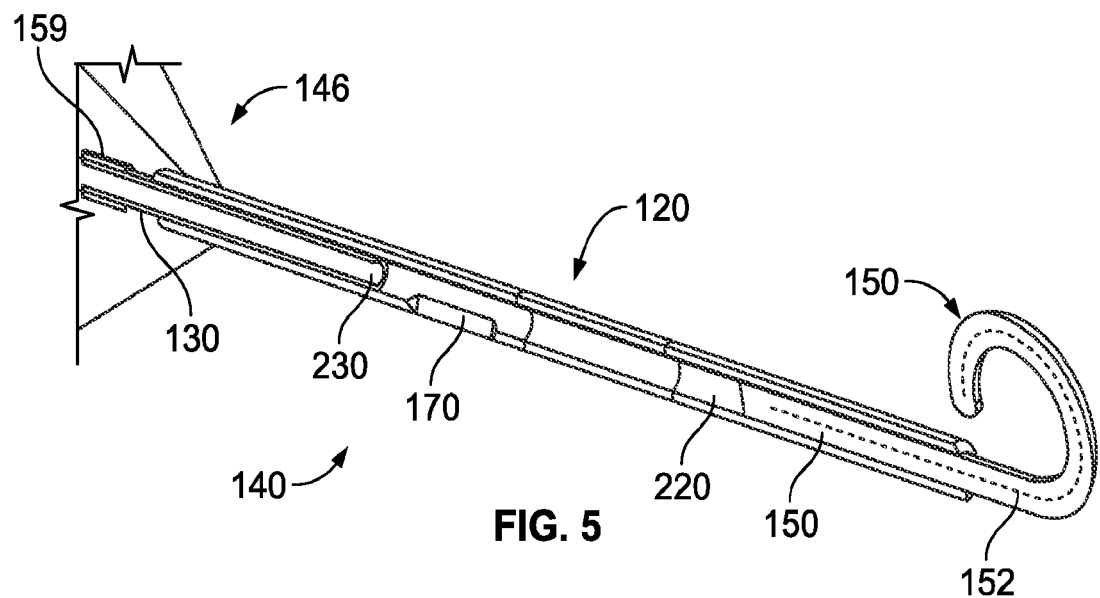
FIG. 5 is a perspective longitudinal cross-sectional view taken along line 5-5 of FIG. 4.

The third catheter member 130 is depicted more particularly in FIGS. 4-5. Third catheter member 120 is coupled at its proximal end to a distal end of the first catheter member 130. A second port 170 passes through a side wall of the third catheter member and communicates between the third lumen 220 and external the occlusion catheter system 100. The distal end of the first catheter member positioned within the third lumen 220 terminates proximal to the second port 170 such that a continuous fluid flow pathway is formed between the first lumen 230, the third lumen 220 and the second port 170 to either introduce fluid or withdraw fluid through the second port 170. It will also be understood by those skilled in the art that maintaining fluid communication between the first lumen 230, the second lumen 220 and the second port 170 also permits introduction of tethered sensors, such as flow sensing wires, pressure sensing wires or the like into and through the first lumen 230 and the third lumen 220 to a position proximate to the second port 170.

Finally, a guiding atraumatic tip 150 is coupled to a distal end section of the third catheter member 120. The guiding atraumatic tip 150 may be made of an elastic, shape memory and/or superelastic material, such as a metal or polymer. A reinforcing member 152 (depicted in phantom) may optionally be included either within the guiding atraumatic tip 150 or wound about an external surface of the guiding atraumatic tip 150 to offer additional reinforcement to the tip 150. A proximal end of the guiding atraumatic tip 150 is coupled to a distal end of the third lumen 220 of the third catheter member 120 and a distal end of the guiding atraumatic tip 150 projects distally from the third catheter member 120 and preferably has a generally circular configuration curving proximally and then toward a central longitudinal axis of the occlusion catheter system 100, but leaving a unconnected end of the distal end of the guiding atraumatic tip 150 to permit the tip 150 to assume a linear configuration co-axial with the central longitudinal axis of the occlusion catheter system 100 for delivery.

In a first embodiment of the inventive occlusion catheter system 100 illustrated in FIGS. 1-8, the occlusion catheter system 100, when the expandable member 140 is in an unexpanded condition, is of sufficiently small cross-segmental dimension to pass through a 6 French (2 mm) percutaneous sheath. It will be understood by those skilled in the art that the occlusion catheter system 100 is not limited to a dimension sufficient to pass through a 2 mm (6 French) percutaneous sheath, but that such lower profile or smaller is generally considered desirable to enable percutaneous introduction of the occlusion catheter system 100 and ease of navigation through tortuous vasculature and to a desired position within the body for purposes of vascular occlusion. The occlusion catheter system 100 is, therefore, not intended to be limited to this dimensional size, but may be made of smaller or larger dimension as desired or needed depending upon the site of required occlusion within the body.

In one embodiment of the invention, the first catheter member 130 is formed of stainless steel metal and is radio opaque. In accordance with another embodiment of the invention, the first catheter member 130 of nitinol. In accordance with yet another embodiment of the invention the first catheter member 130 formed of biocompatible polymers. It still yet another embodiment of the invention the first catheter member 130 is made of a metal reinforced polymer. The first catheter member 130 lends column strength to the occlusion catheter system 100 and provides a functional backbone for carrying the second catheter member 110, the third catheter member 120 and the expandable occlusion balloon.

Figure 7:
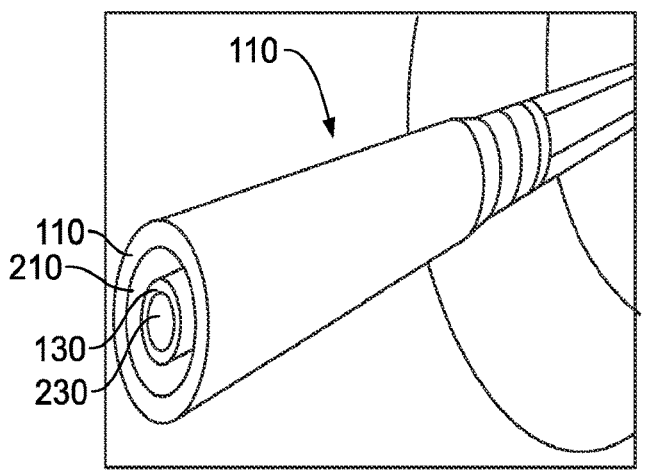
FIG. 7 is a partial cross-sectional end view of a proximal hub of the occlusion catheter of the present invention.
Figure 8:
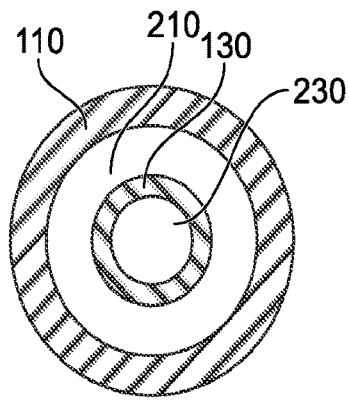
FIG. 8 is a transverse cross-sectional view taken along line 8-8 of FIG. 1 and line 8-8 of FIG. 6.

The outer diameter of the first catheter member 130 is smaller than the inner diameter of the second lumen 210 of the second catheter member 110 thereby forming an annular space 212 between the outer surface of the first catheter member 130 and the inner surface of the second catheter member 110 210 (FIGS. 7-8).

In one embodiment of the invention, the distal end of the second catheter member 110 may have a tapering or narrowing diameter of the outside surface and/or the second lumen 210 diameter. Preferably, there is a minimal amount of narrowing on the second catheter member 110 and the proximal lumen 210 to allow the annular space 212 to remain sufficiently large down the length of the second catheter member 110 to permit adequate flow of the inflation fluid through the annular space 212.

Turning now to FIGS. 4-5, the distal portion of the occlusion catheter system 100 is illustrated. The first lumen 230 of the first catheter member 130 may be used as a pressure monitoring line, such as by using a fluid column therein to sense pressures through the second port 170; alternatively, the first lumen 230 may be used to introduce or withdraw fluids, such as drugs, contrast media or blood through the second port 170. Referring to FIG. 5, the outer surface of the first catheter member 130 is coupled to at least a portion of the inner surface of the distal lumen 220, such that there is no annular space between the outer surface of the first catheter member 130 and the inner surface of the second lumen 220. In one embodiment, the portion of the inner surface of the distal lumen 220 may be the length of the second lumen 220. Referring now to FIG. 4, the third catheter member 120 may include a plurality of segments of distally decreasing durometer polymer to provide a stepdown transition to the guiding atraumatic tip 150. The number of step down durometer segments may be between 1 and 6 and may step down in decreasing fashion by regular or irregular increments, such, for example 75D, 63D, 55D, 40D, etc. Alternatively, the third catheter member 120 may be made of a single durometer polymer, but having distally tapering wall thicknesses to impart a flexibility gradient to the third catheter member 120. The plurality of segments of decreasing durometer plastic may be abutted and be bonded together or may be manufactured from a single extrusion including decreasing durometer strengths. Still further, the third catheter member 120 may be fabricated in such a manner as to have varying hardness of the polymer material along the longitudinal length of the third catheter member 120 in combination with varying wall thickness along its longitudinal length. For example, as the wall thickness along the longitudinal length lessens, the hardness of the polymer material may also decrease. Alternatively, as the wall thickness along the longitudinal length of the third catheter member lessens, the hardness of the polymer material may be selected to increase. Thus, there may be a linear relationship or an inverse relationship between wall thickness of the third catheter member and the hardness of the polymer forming the third catheter member.

As depicted in FIGS. 4-5, the guiding atraumatic tip 150 is shown in its unstrained and undeformed state as it would assume when in the body. The guiding atraumatic tip 150 is used to minimize trauma to or perforation of the vasculature as the occlusion catheter system 100 is advanced through the patient's tortuous anatomy. The size, shape and material of the distal section of the tip 150 are such that it will not pass into collateral vessels during delivery. The guiding atraumatic tip 150 has a constrained state when passing through an introducer sheath in which the distal section of the tip 150 is substantially linear and co-axial with the longitudinal axis of the occlusion catheter system 100, and a relaxed state, as depicted, which is assumed upon exiting the introducer sheath and entering a blood vessel. As also described with reference to an alternative embodiment of the guiding atraumatic tip 450 described with reference to FIGS. 10-11, below, in its unstrained and undeformed state, the guiding atraumatic tip 150 consists generally of a polymeric cylindrical or tubular member that has a distal section that has been formed, such as by molding, into a curved section that forms an incomplete circle that project proximally toward the proximal end of the occlusion catheter system 100. The distal section has a distally extending section that first projects distally and a curved section continuous with the distally extending section that curves away from the central longitudinal axis of the occlusion catheter system 100, then proximally toward the occlusion member and subtends an incomplete generally circular arc toward the central longitudinal axis of the occlusion catheter system 100. The angle of the curve may be between 270 degrees to 1080 degrees, desirably the curve is between about 300 degrees and 350 degrees such that a gap is provided between a terminal end of the distal section and a more proximal portion of the distal section. It will also be understood that the distally extending section and curved section may be formed as a generally in plane circular shape or may be formed as an out-of-plane generally helical shape, where a terminal end of the curved section is laterally displaced from the central longitudinal axis of the occlusion catheter system 100.

The guiding atraumatic tip 150 may be formed of elastomeric, shape memory or superelastic material, including metals and polymer. The guiding atraumatic tip 150 may optionally also have a reinforcing elastic, shape memory or superelastic core 152 which aids in transition between the unstressed state and the stressed state of the guiding atraumatic tip 150. In accordance with an exemplary embodiment of the tip 150, the largest outer diameter of the guiding atraumatic tip 150 may be between 1-7 mm, preferably between 2-6 mm and most preferably between 4-6 mm.

The guiding atraumatic tip 150 is joined to the third catheter member 120 by engaging a proximal section of the atraumatic tip 150 within the third lumen 220 of the third catheter member 120 and creating a bond between the two elements, such as by thermal welding, thermal reflow, adhesive or other biocompatible methods of joining catheter components as is generally known to those skilled in the field to which this invention pertains.

Figure 6:
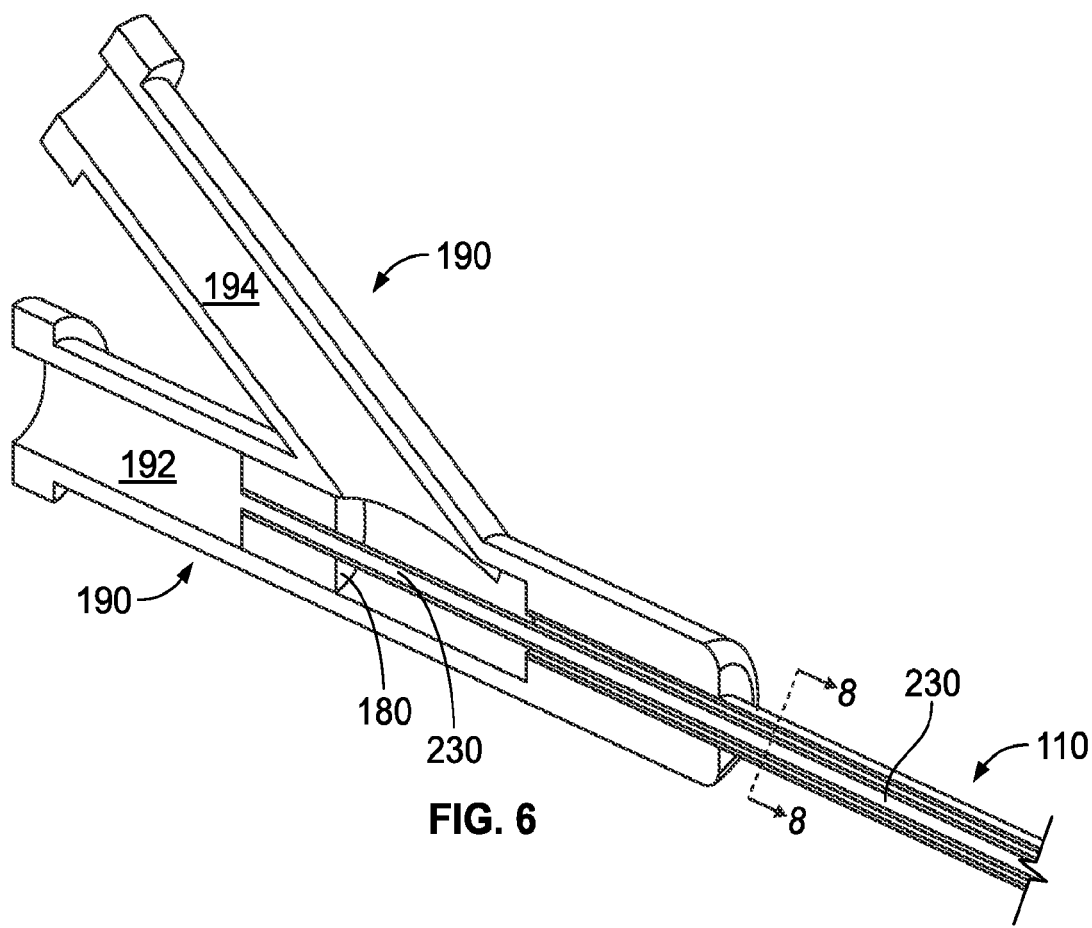
FIG. 6 is a cross-sectional view taken along line 6-6 of FIG. 1.

Turning now to FIGS. 6-8, a proximal portion of the occlusion catheter system 100 and the proximal hub 190 are illustrated. The second catheter member 110 is coupled to the proximal hub 190 and the distal end of the first catheter member 130 may be operably coupled to the proximal hub 190 at a proximal bonding site using an adhesive 180 to bond an inner wall surface of the proximal hub 190 to an outer wall surface of the first catheter member 130. As illustrated, the proximal hub 190 has two fluid pathways 192 and 194. A first fluid pathway 192 communicates with the first lumen 230 of the first catheter member and a second fluid pathway 194 communicates with the second lumen 210 of the second catheter member 120. It will be understood that the proximal hub 190 may be configured to have more than two fluid pathways, with each fluid pathway communicating with a different lumen in the occlusion catheter system 100. The first fluid pathway 192 of the proximal hub 190 may be connected to an external pressure sensor, which would transduce pressure from a fluid column within the first lumen 230 and through the second port 170 (FIG. 5).

Turning now to FIGS. 9 and 9A-9D, an alternative embodiment of the occlusion catheter system 300 is illustrated. Like the occlusion catheter system 100, occlusion catheter system 300 generally includes a catheter assembly including a first catheter member 310 having at least two lumens 210, 330 passing longitudinally through the first catheter member 310, a second catheter member 320 having a single lumen 230 passing longitudinally through the second catheter member 320 and an expandable occlusion member 140. Expandable occlusion member 140 may be an inflatable balloon or may be another expandable member capable of occluding a vessel. The first catheter member 310 is coupled at its proximal end to a proximal hub 190 (not shown) and at a distal end thereof to a proximal end of the expandable occlusion member 140. The second catheter member 320 is coupled at its distal end to a proximal end of the first catheter member 310 such that one of the first lumen 210 or the second lumen 330 is in fluid flow communication with the second catheter member 320. The other of the first lumen 210 or the second lumen 230 terminates at the distal end of the first catheter member 310. For purposes of illustration only and for clarity in the following description, it will be assumed that second lumen 330 terminates at the distal end of the first catheter member 310 and has a distal port opening 160, it will also be assumed that the first lumen 210 is in fluid flow communication with the second catheter member 320. As with the first embodiment of the occlusion catheter system 100 described above, the second embodiment of the occlusion catheter system 300, when the occlusion member 140 is in an contracted state, it is of a sufficiently small cross-sectional diameter to pass through a 6 French (2 mm) percutaneous sheath. It will be understood by those skilled in the art that the occlusion catheter system 300 is not limited to a dimension sufficient to pass through a 2 mm (6 French) percutaneous sheath, but that such lower profile or smaller is generally considered desirable to enable percutaneous insertion and removal and passage through tortuous vasculature and to a desired position within the body for purposes of vascular occlusion. The occlusion catheter system 300 is, therefore, not intended to be limited to this dimensional size, but may be made of smaller or larger dimension as desired or needed.

Figure 9:
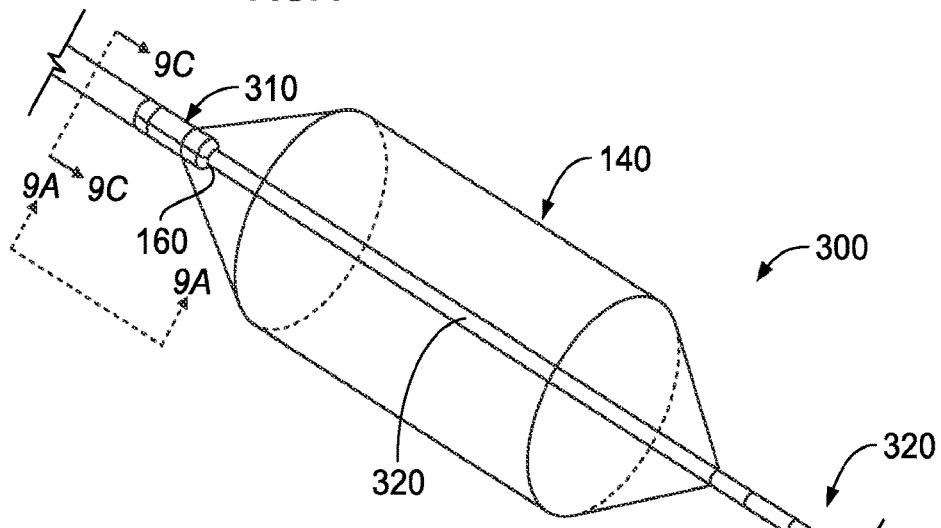
FIG. 9 is a perspective view of an alternative embodiment of the inventive occlusion catheter.
Figure 9A:
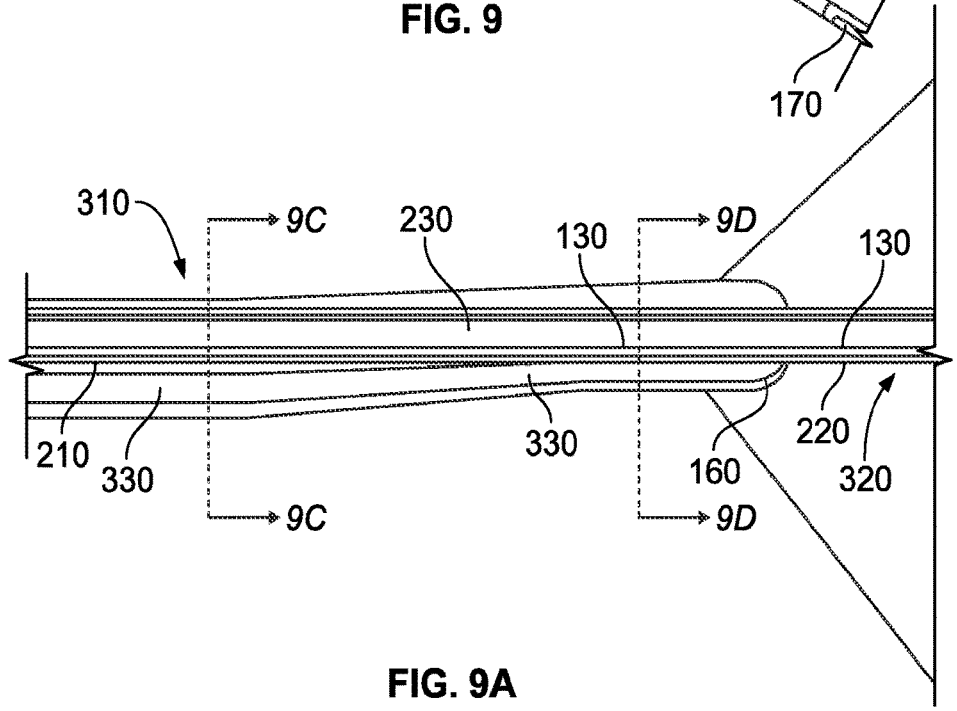
FIG. 9A is a cross-sectional view taken along line 9A-9A of FIG. 9.
Figure 9B:
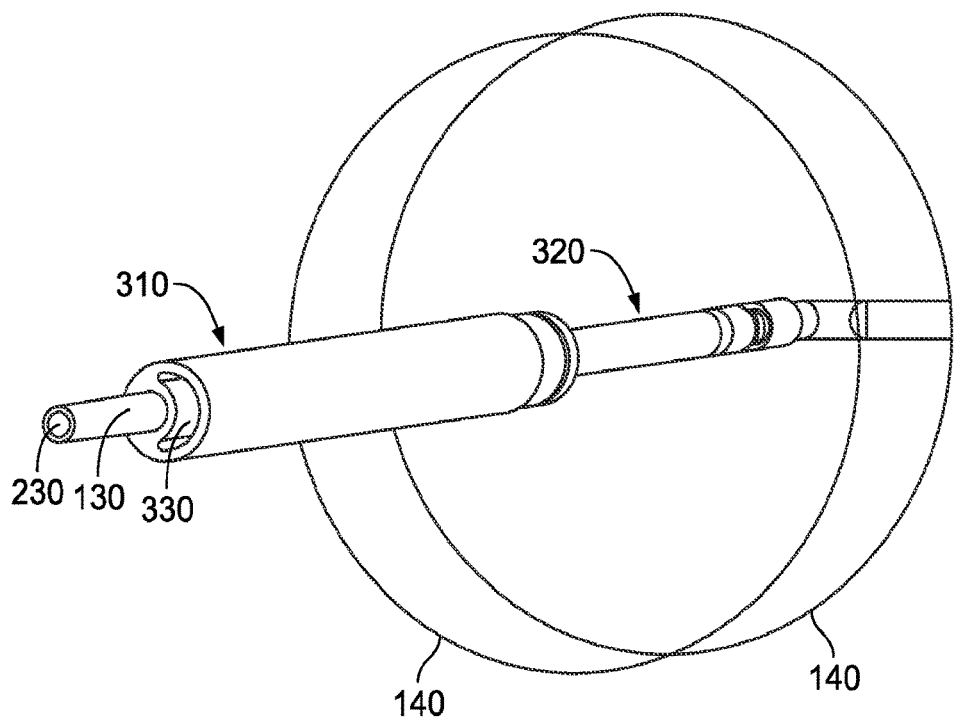
FIG. 9B is a partial cross-sectional end view of FIG. 9.

Referring now to FIG. 9A, the first catheter member 310 includes first lumen 330 and a second lumen 210. The second catheter member 320 includes a first lumen 220. The first catheter member 310 terminates at its distal end within the space defined under the balloon 140, where it is both coupled to the second catheter member 320 and terminates with an open port 160 in fluid communication with lumen 330, permitting fluid to be delivered to and from the balloon 140 for inflation and/or deflation. In accordance with an alternative embodiment, the distal end of the first catheter member 310 may, optionally, be tapered, such as by narrowing the wall thickness of the catheter member 310 or by crimping the first catheter member 310 to a smaller diameter, thereby compressing and reducing the open area of the first lumen 330 and the second lumen 210. If the first catheter member 310 is crimped to a tapered diameter, it is preferable that the extent of the crimping does not compress the open area of the first lumen 330 and the second lumen 210 in a manner that significantly reduces fluid flow there through of fluid flow pressures therein, particularly with the second lumen 330 when it is used for the inflation fluid for the inflation balloon 140.

Figure 9C:
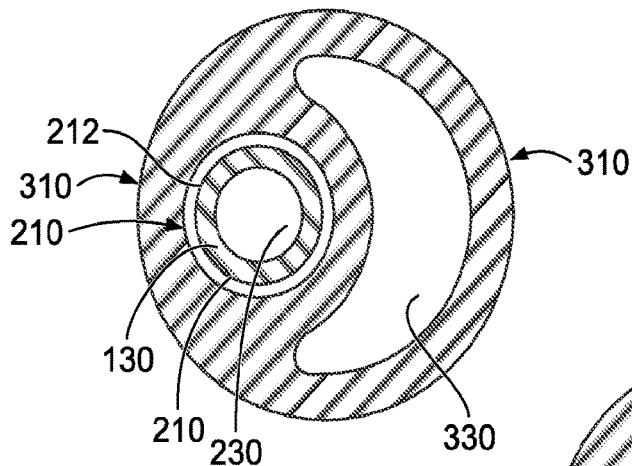
FIG. 9C is a cross-sectional view taken along line 9C-9C of FIG. 9

The third catheter member 130 is positioned within one of the first lumen 210 or the second lumen 330 of the first catheter member 310. As depicted in the figures this arrangement is illustrated with the third catheter member 130 being positioned within the first lumen 210 of the first catheter member 310 and also within the first lumen 220 of the second catheter member 320. The outer diameter of the third catheter member 130 is less than the inner diameter of the first lumen 210 of the first catheter member 310 as well as smaller than the inner diameter of the first lumen 210 of the second catheter member 320, such that an annular space 212 is formed there between as depicted in FIG. 9C. In the more distal region of the first catheter member 310, within the region of the distal taper discussed above, the annular space 212 is compressed and either closes or is substantially closed to fluid flow, thereby effectively sealing the distal end of the first lumen 210 near the transition to the proximal attachment point of the expandable occlusion balloon 140, as depicted in FIG. 9A.

The third catheter member 130 passes longitudinally into the first lumen 230 of the second catheter member 320 and has a first lumen 230 passing longitudinally through the third catheter member 130. As with the first catheter member 130 of the first alternative embodiment described above, the first lumen 230 of the third catheter member 130 permits monitoring of conditions within the body, such as arterial pressure monitoring by hydrostatic pressure within a fluid column within the first lumen 230, or allows for the introduction of tethered sensors, such as flow sensing wires, pressure sensing wires or the like to the distal end of the occlusion catheter system 300. First lumen 230 may also be used to deliver drugs, contrast media, or permit the introduction or withdrawal of fluids to and from the body.

Figure 9D:
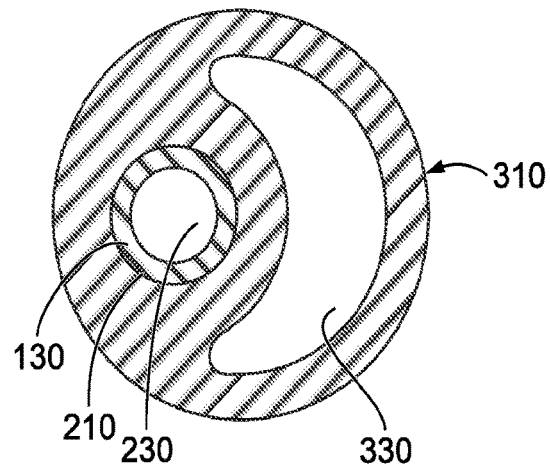
FIG. 9D is a cross-sectional view taken along line 9D-9D of FIG. 9.

As with the alternative embodiment discussed above with reference to FIGS. 1-8, the embodiment depicted in FIGS. 9-9D may, optionally, include the second catheter member 320 being constructed of plural segments having distally increasing flexibility, such as by making the segments of distally decreasing durometer polymer or fashioning the second catheter member 320 to have a distally tapering wall thickness. The second catheter member 320 may be formed of discrete segments abutted and coupled together to form an elongated second catheter member 320 with either distally decreasing durometers or distally tapering wall thicknesses. Alternatively, the second catheter member 320 may be made by extrusion or molding polymers of distally decreasing Durometer, distally tapering wall thicknesses or combinations thereof As with the alternative embodiment of the occlusion catheter system 100, the second catheter member 320 includes an open port 170 that is in fluid flow communication with the first lumen 230 of the third catheter member. Similarly, as with the occlusion catheter system 100, occlusion catheter system 300 includes a guiding atraumatic tip (not shown in FIGS. 9-9D) as described above with reference to guiding atraumatic tip 150, which is joined to a distal end of the second catheter member 320.

Figure 10:
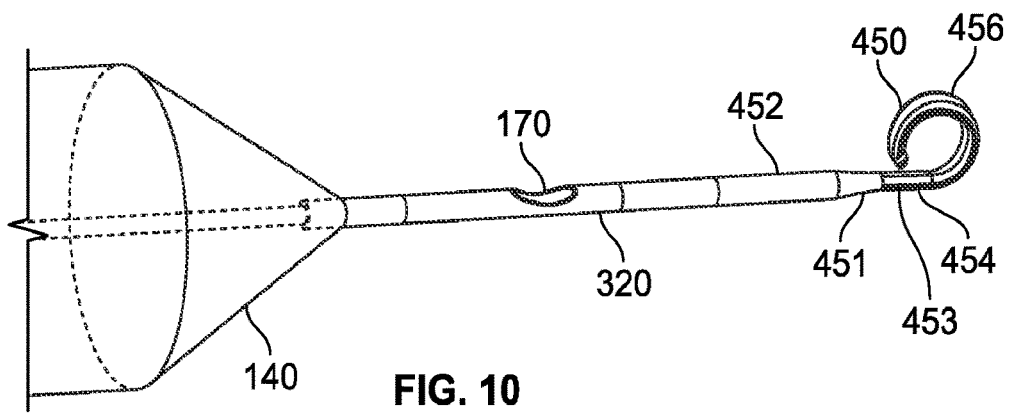
FIG. 10 is a perspective view of another alternative embodiment of the inventive occlusion catheter depicting an alternative embodiment of a guiding atraumatic tip.
Figure 11:
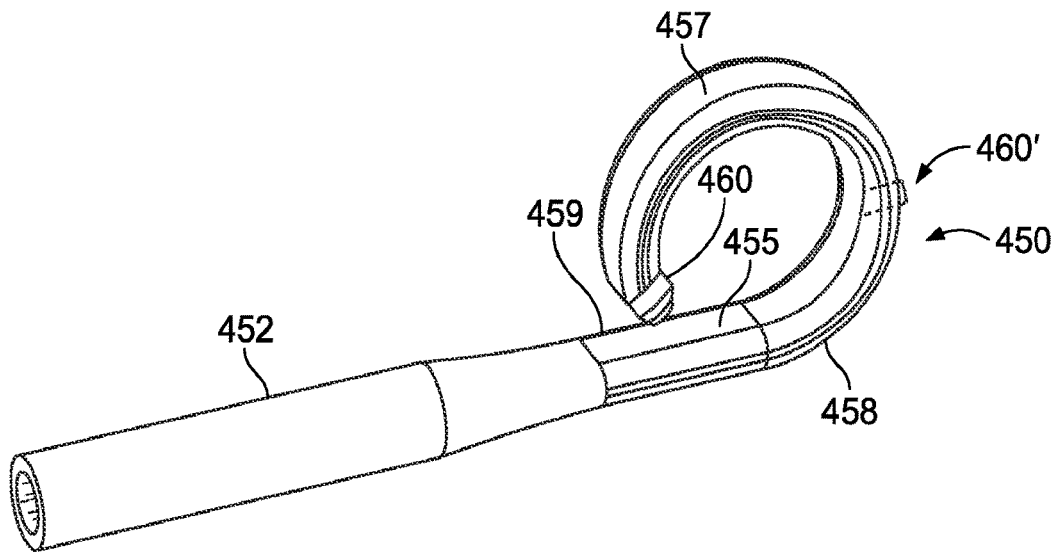
FIG. 11 is an enlarged perspective view of the alternative embodiment of the guiding alternative tip of FIG. 10.
Figure 13:
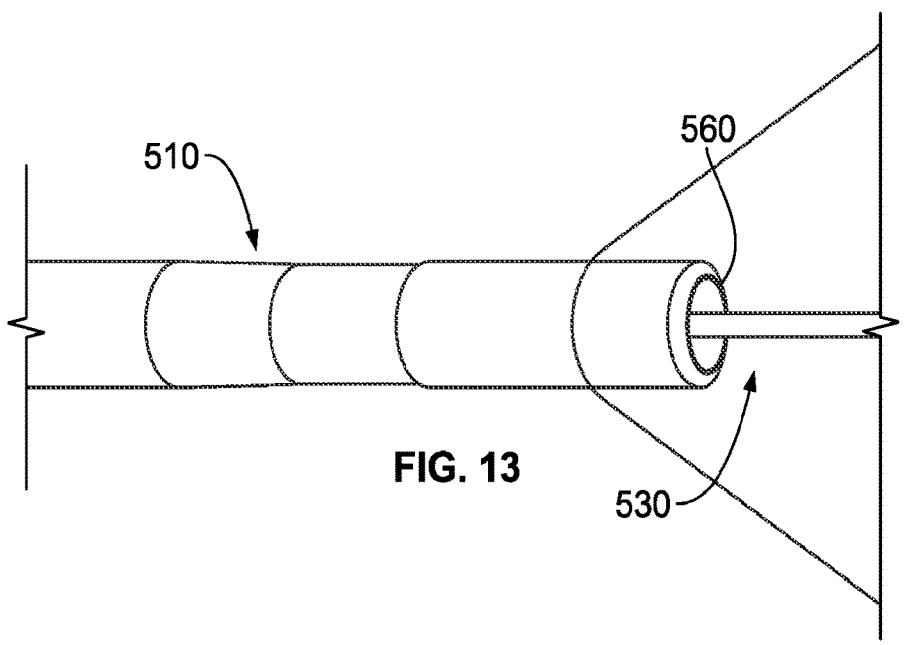
FIG. 13 is an enlarged perspective view of the first port of the inventive occlusion catheter depicted in FIG. 12.
Figure 12:
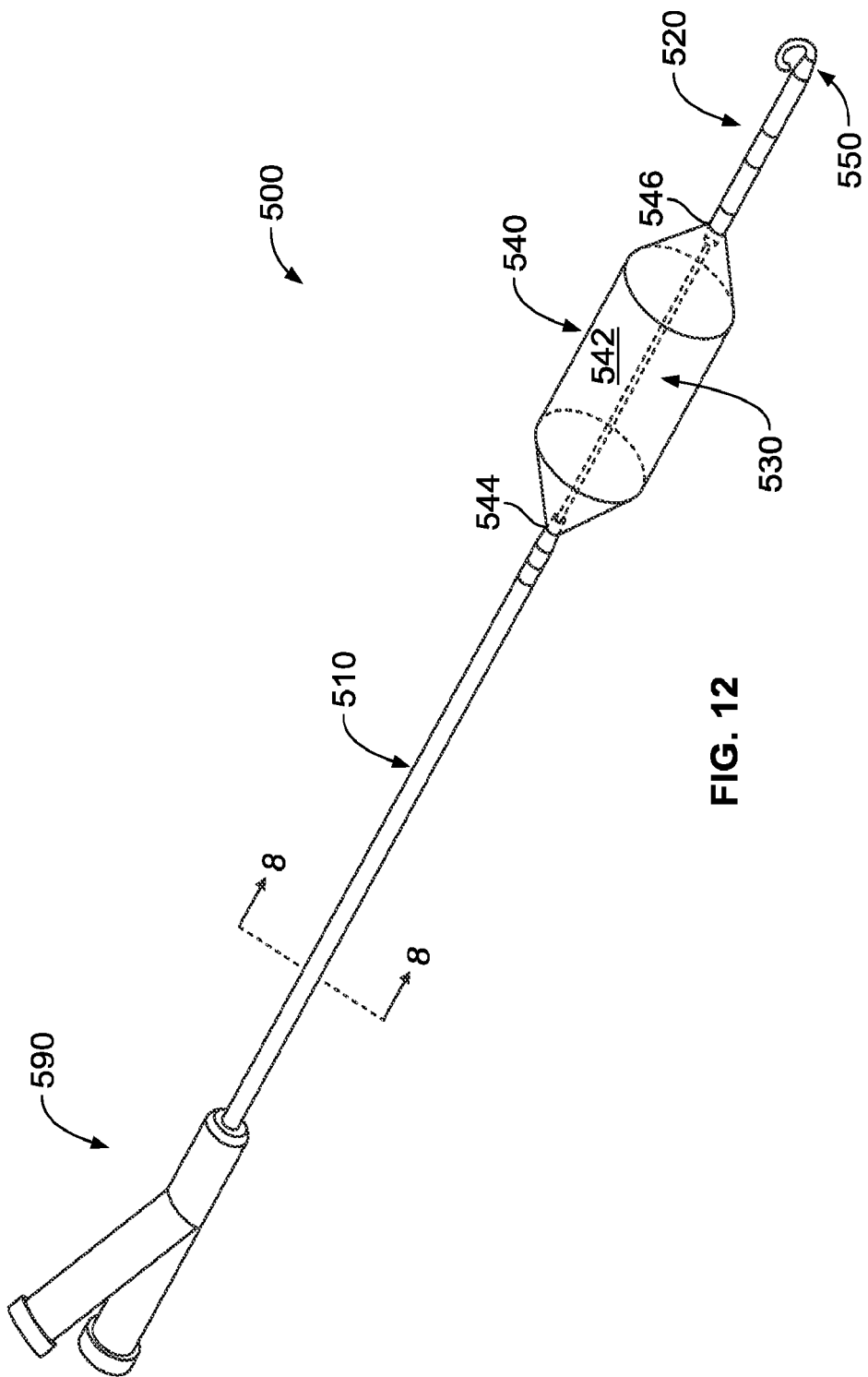
FIG. 12 is a perspective view of another embodiment of a occlusion catheter described herein.

With reference to FIGS. 10 and 11, there is depicted an alternative embodiment of the guiding atraumatic tip 450. It will be understood that guiding atraumatic tip 450 may be employed with any of the foregoing embodiments of the inventive occlusion catheter system 100 or of the inventive occlusion catheter system 300. Guiding atraumatic tip 450 consists generally of a polymeric cylindrical or tubular member 452 that has a distal section 454 thereof that has been formed, such as by molding or extrusion, into a generally flattened shape having at least two generally planar opposing surfaces 455, 457. Depending upon the formation process, two generally radiused curved opposing surfaces 458, 459 may also be formed during the formation process. The distal section 454 has a distally extending section 453 that projects distally and a curved section 456 continuous with the distally extending section that curves away from the central longitudinal axis of the occlusion catheter system 100, 300 then proximally toward the occlusion balloon and subtends a generally circular arc toward the central longitudinal axis of the occlusion catheter system 100, 300. The angle of the curve may be between 270 degrees to 1080 degrees, desirably the curve is between about 300 degrees and 350 degrees such that a gap is provided between the terminal end of the generally cylindrical flattened distal section 454 and the more proximal surface of the distal section 454. It will also be understood that the distally extending section 453 and curved section 456 may be formed as a generally in plane circular shape or may be formed as an out-of-plane generally helical shape, where a terminal end of the curved section 456 is laterally displaced from the central longitudinal axis of the occlusion catheter system 100 or occlusion catheter system 300. In this manner, the generally flattened distal section 454 is characterized by a generally circular, proximally oriented bend that operates in a manner similar to the guiding atraumatic tip 150 or guiding atraumatic tip 350, but is made of a polymer material without the need for a reinforcing member 152 as described above.

A tapered transition section 451 may, optionally, be provided between the polymeric cylindrical or tubular member 452 and the generally flattened distal section 454. Guiding atraumatic tip 450 may be integral with the third catheter member 120 of occlusion catheter system 100 or the second catheter member 320 of occlusion catheter system 300. Alternatively, guiding atraumatic tip 450 may be fabricated as a discrete member and joined to the third catheter member 120 of occlusion catheter system 100 or the second catheter member 320 of occlusion catheter system 300.

The guiding atraumatic tip 450 may be made of PEBAX having a durometer of 40, or a similar polymer, such polyurethane, that matches the catheter shaft and balloon to make bonding easier and more secure. As discussed above, the longitudinal flexibility of guiding atraumatic tip 450 may be manipulated by varying the thickness, the hardness or both properties of the curved distal section of the guiding autraumatic tip 450. Thus the curved distal section 456 may have a hardness of 40D (Shore Durometer), while the proximal section of the guiding atraumatic tip 450 may have a higher hardness, such as 72D (Shore Durometer). As discussed above, the guiding atraumatic tip 450 may be either cylindrical or tubular, or have a solid cylindrical section and a tubular section. The curve of the guiding atraumatic tip 450 may be made by any of a wide number of processes, including, for example, injection molding, round extrusion, flattening and post-processing into the curved distal section 456, a flat extrusion bonded to a round extrusion, or an extrusion that is pressed into a hot die having a shape of the desired curved distal section 450.

The atraumatic tip 450 may include a radio opaque tip marker 460. The radio opaque tip marker 460 may be implemented as a band surrounding the tip 450 or as a two-dimensional planar material on one or both of the planar opposing surfaces 455. Alternatively, the radio opaque tip marker 460 may be located at the most distal point of the atraumatic tip 450 indicated at 460' in FIG. 11. The band or the planar material may be composed of any suitable radio opaque material, such as for example, stainless steel or a suitable alloy such as platinum iridium. In another example embodiment, the tip 450 may be made of a plastic or polymer, such as for example, PEBAX that is impregnated or doped with a radio opaque material. In another example embodiment, the plastic or polymer composition forming the tip 450 may be mixed with a radio opaque compound such as, for example, barium sulfate sufficient to permit visualization of the tip 450 using X-ray or fluoroscopy.

In an alternative embodiment described herein with reference to FIGS. 12-18, a occlusion catheter system 500 generally includes a catheter assembly having a solid wire 530, an inflation catheter member 510 having an inflation lumen 610, a distal catheter member 520, an expandable occlusion balloon 540, a proximal hub 590 and a guiding atraumatic tip 550. The solid wire 530 extends longitudinally through the inflation catheter member 510, and is coupled at its proximal end to the proximal hub 590 and at its distal end to a proximal section of the distal catheter member 520. The inflation lumen 610 of the inflation catheter member 510 also extends longitudinally through the inflation catheter member 510, and terminates in a first port 560 distal to a proximal end of and within a space 542 defined by the expandable occlusion balloon 540, such that the inflation lumen 610 is in fluid flow communication with the space 542 within the expandable occlusion balloon 540 to convey an inflation fluid to and from the expandable occlusion balloon 540 from a source external the occlusion catheter system 500. The distal catheter member 520 is coupled at a proximal end thereof to a distal end of the solid wire 530. The inflation catheter member 510 and the distal catheter member 520 are positioned in longitudinal co-axial spaced apart relationship from one and other along a longitudinal axis of the solid wire 530 thereby defining an intermediate region of the solid wire 530 within the space 542 within the expandable occlusion balloon 540 that is not covered by either the inflation catheter member 510 or the distal catheter member 520.

In general, the alternative embodiment described herein with reference to FIGS. 12-18 includes a wire 530 instead of a tube with a lumen. The wire 530 may be implemented as a solid flexible wire made of any suitable material that may be formed into a wire-like component, or may be a solid wire reinforced with an outer wire winding or windings. Examples of materials that may be used for the solid flexible wire include nitinol and stainless steel. The wire 530 implementation without a lumen eliminates the fluid communication with a third lumen having sensors thereby removing the elements used to implement the sensing function in the catheter system 100 described above with reference to FIGS. 1-8. The wire 530 does, however, allow for the achieving a lower profile for the catheter system.

Referring to FIGS. 12-18, the expandable occlusion balloon 540 is attached, at its proximal end 544 to a distal end of the inflation catheter member 510 and at its distal end 546 to a proximal end of the distal catheter member 520. In operation, expandable occlusion balloon 540 is inflated by introducing an inflation fluid, such as saline, from an external source, such as a syringe, coupled to the proximal hub 590, into and through the inflation lumen 610, out of the first port 560 and into the space 542 within the expandable occlusion balloon 540. Inflation and deflation of the expandable occlusion balloon 540 in FIGS. 1-8 is performed as described above with reference to FIGS. 1-8.

Figure 15:
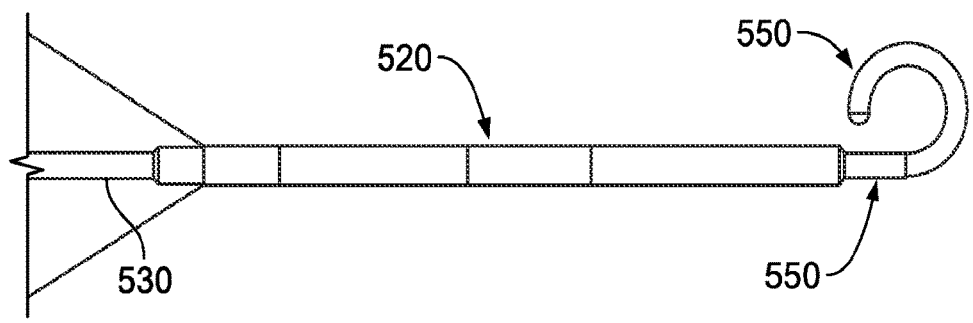
FIG. 15 is a perspective view of a distal section of the inventive occlusion catheter depicted in FIG. 12
Figure 16:
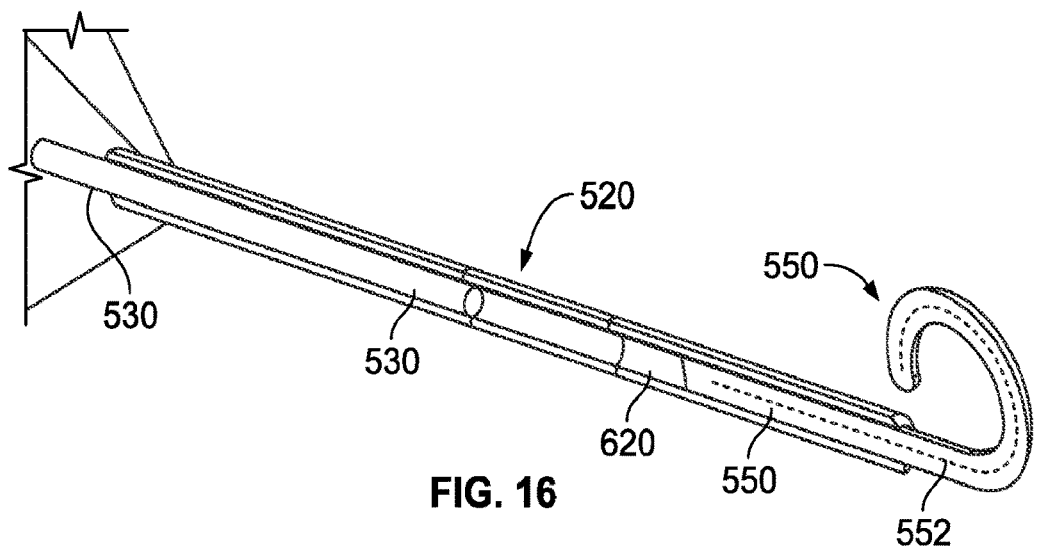
FIG. 16 is a perspective longitudinal cross-sectional view taken along line 16-16 of FIG. 15.

Referring to FIGS. 15 and 16, the third catheter member 520 is fixedly coupled at its proximal end concentrically about a distal end of the solid wire 530. In the example shown in FIG. 16, the distal catheter member 520 has a lumen 620 extending longitudinally through the distal catheter member and coupled concentrically about a proximal end of the atraumatic tip 550. The guiding atraumatic tip 150 may be made of an elastic, shape memory and/or superelastic material, such as a metal or polymer. A reinforcing member 552 (depicted in phantom) may optionally be included either within the guiding atraumatic tip 550 or wound about an external surface of the guiding atraumatic tip 550 to offer additional reinforcement to the tip 550. A distal end of the guiding atraumatic tip 550 projects distally from the distal catheter member 520 and preferably has a generally circular configuration curving proximally and then toward a central longitudinal axis of the occlusion catheter system 500, but leaving a unconnected end of the distal end of the guiding atraumatic tip 550 to permit the tip 550 to assume a linear configuration co-axial with the central longitudinal axis of the occlusion catheter system 500 for delivery.

As noted above in the description of the first embodiment of the inventive occlusion catheter system 100 illustrated in FIGS. 1-8, the occlusion catheter system 100, when the expandable occlusion member 140 is in an unexpanded state, it is of sufficiently small cross-segmental dimension to pass through a 6 French (2 mm) percutaneous sheath. It will be understood by those skilled in the art that example implementations of the occlusion catheter system 500 described herein with reference to FIGS. 12-18 may have an even smaller cross-sectional dimension due to the use of a solid wire 530 instead of a catheter with a lumen. The diameter of the solid wire 530 is smaller than the inner diameter of the inflation lumen 610 of the inflation catheter member 510 thereby forming an annular space 612 between the outer surface of the solid wire 530 and the inner surface of the inflation catheter member 510. The dimensions of the inner diameter of the inflation lumen 610 and the diameter of the solid wire 530 may be specified in example implementations to provide optimal inflation fluid flow as well as a reduced profile that may further ease deployment.

Figure 14:
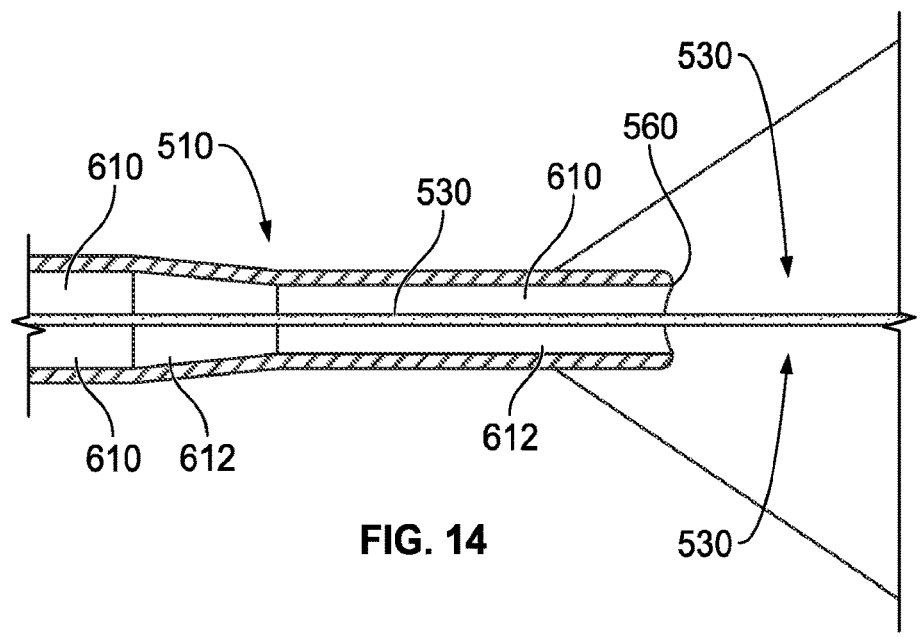
FIG. 14 is a longitudinal cross-sectional view of FIG. 13.

Turning now to FIGS. 14-16, the distal portion of the occlusion catheter system 500 is illustrated. As shown in FIG. 16, the outer surface of the solid wire 530 is coupled to at least a portion of the inner surface of the second lumen 620, such that there is no annular space between the outer surface of the solid wire 530 and the inner surface of the second lumen 620. Referring now to FIG. 15, the distal catheter member 520 may include a plurality of segments of distally decreasing durometer polymer to provide a step-down transition to the guiding atraumatic tip 150. The number of step down durometer segments may be between 1 and 6 and may step down in decreasing fashion by regular or irregular increments, such, for example 75D, 63D, 55D, 40D, etc. Alternatively, the distal catheter member 520 may be made of a single durometer polymer, but having distally tapering wall thicknesses to impart a flexibility gradient to the third catheter member 520. The plurality of segments of decreasing durometer plastic may be abutted and be bonded together or may be manufactured from a single extrusion including decreasing durometer strengths, wall thicknesses, or combinations thereof.

In an alternative embodiment, the wire 530 extends completely into the space shown for the second lumen 620 such that the distal catheter member 520 completely covers the distal end of the wire 530. The atraumatic tip 550 may also be formed as an extension of the second catheter body 520 rather than as a separate member joined of the second catheter body 520.

Figure 17:
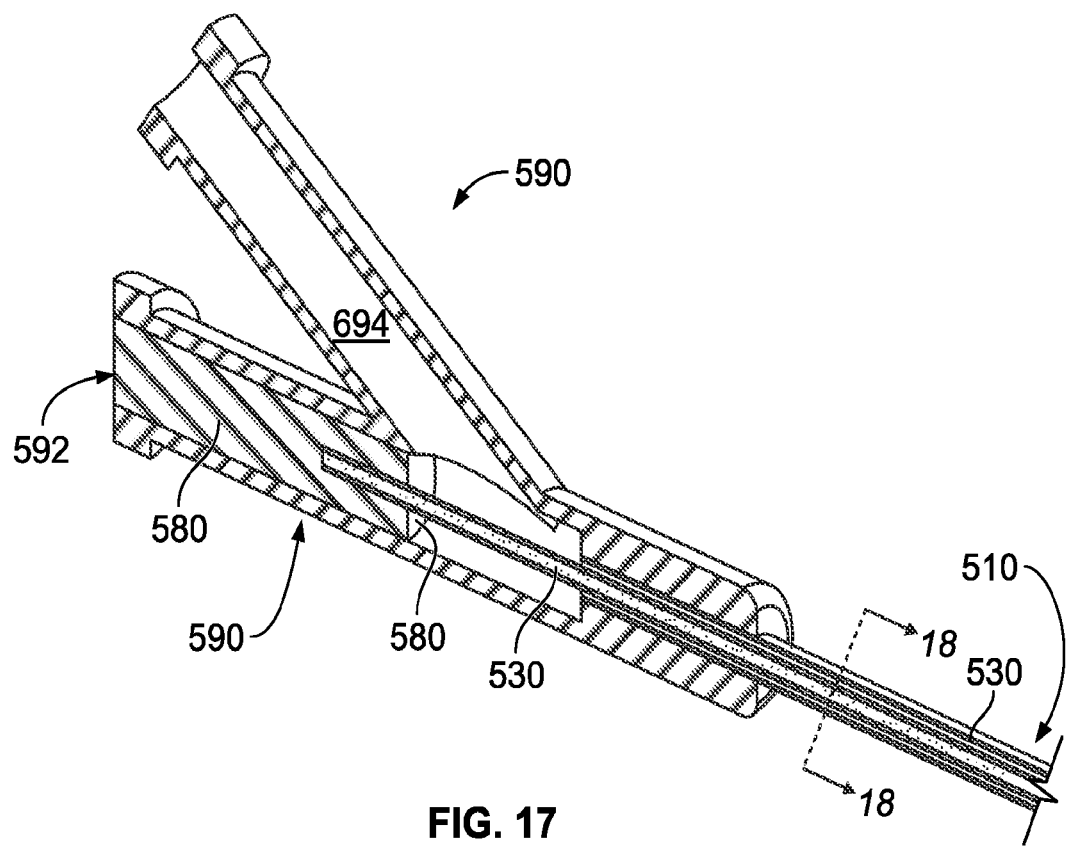
FIG. 17 is a cross-sectional view taken along line 17-17 of FIG. 12.
Figure 18:
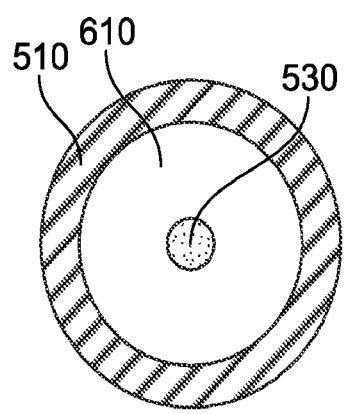
FIG. 18 is a transverse cross-sectional view taken along line 18-18 of FIG. 1 and line 18-18 of FIG. 6.

Turning now to FIG. 17, the proximal portion of the occlusion catheter system 500 is illustrated. The inflation catheter member 510 is coupled to the proximal hub 590 and the distal end of the solid wire 530 is fixedly coupled to the proximal hub 590 at a proximal bonding site using an adhesive 580 to bond an inner wall surface of the proximal hub 590 to an outer wall surface of the solid wire 530. The amount of adhesive 580 used should be sufficient to fixedly couple the solid wire 530 to the proximal hub 590. As shown in FIG. 17, the adhesive 580 may fill the entire portion 592 of the proximal hub 590 that holds the solid wire 530. Since the solid wire 530 has no lumen, no fluid pathway is needed in the portion 592 that holds the solid wire 530. As illustrated, the proximal hub 190 has a single fluid pathway 194. The second fluid pathway 194 communicates with the inflation lumen 610 of the inflation catheter member 520. It will be understood that the proximal hub 590 may be configured to have more than a single fluid pathway, with each fluid pathway communicating with a different one of any additional lumens in the occlusion catheter system 500.

It will be understood that when reference is made to coupling two or more component pieces of the occlusion catheter system, that conventional catheter material bonding modalities are intended to be encompassed and employed. For example, a wide variety of biocompatible adhesives useful in catheter manufacture are known, similarly, thermobonding techniques used in catheter manufacture are also known. Thus, for example, where it is described that the guiding atraumatic tip is coupled to the third catheter member or to the distal catheter member, it is contemplated that such coupling may be made using thermobonding, biocompatible adhesives or other methods of fixedly bonding two components in medical devices.

It will also be understood by those skilled in the art that it is well known to manufacture catheters of a variety of medical grade, biocompatible polymers, such as, for example and without limitation, silicone, nylon, polyurethane, PETE, latex, thermoplastic elastomers, polyether block amides (PEBAX, Arkema, Paris, France). Alternatively, it is known to manufacture catheters of metals, such as nitinol or stainless steel. Similarly, it is known to manufacture catheters of metal-reinforced polymer, such as, for example and without limitation, stainless steel braiding over polyurethane, stainless steel helical windings over silicone or nitinol reinforced polymer. Thus, any or all of the first catheter member, the second catheter member, the inflation catheter member, the distal catheter member, or the third catheter member in any of the foregoing embodiments may be fabricated of biocompatible polymers, biocompatible metals or metal-reinforced polymers, as is known in the art.

It will also be understood by those skilled in the art that while the implementation of radio opaque markers are described in the context of embodiments described with reference to FIGS. 1-8, it may be desirable to include radio opaque marker bands positioned at the proximal and distal ends of the balloon in implementations of embodiments described above with reference to FIGS. 9-11, and embodiments described above with reference to FIGS. 12-18. It is also desirable to include length markers on the outer catheter shaft to indicate to the physician the insertion depth of the occlusion catheter system 100, the occlusion catheter system 300, or the occlusion catheter system 500. The length markers may be printed or laser etched onto the outside of the catheter shaft.

It will also be understood by those skilled in the art that it is well known to coat the catheters and balloons with a variety of coatings, including without limitation, antibacterial, antimicrobial, lubricants, anticoagulant and/or antifouling coatings. Thus, any or all of the first catheter members, the solid wire, the inflation catheter member, the second catheter member, the distal catheter member, the third catheter member, the expandable occlusion balloon or the guiding atraumatic tip may further include one or more coatings as is known in the art.

What is claimed is:

1. An occlusion catheter system comprising:
    a first catheter member having a first lumen extending longitudinally through the first catheter member and a first opening at a distal end of the first catheter member;
    a second catheter member having a second lumen extending longitudinally through the second catheter member and a second opening at a distal end of the second catheter member, the second catheter member is positioned over and in spaced apart relationship relative to a proximal section of the first catheter member forming an annular space between the second catheter member and the first catheter member and defining an annular port at the distal end of the second catheter member, the proximal section of the first catheter member resides within the second lumen of the second catheter member and the first catheter member extends beyond the distal end of the second catheter member;
    a third catheter member having a third lumen extending longitudinally through the third catheter member, the third catheter member is positioned over a distal section of the first catheter member, the third catheter member having a distal section that extends distally from a distal end of the first catheter member such that the first lumen and the third lumen are in fluid flow communication, whereby the second and third catheter members are spaced apart from each other along a longitudinal axis of the first catheter member with the first catheter member extending there between;
    an atraumatic tip member having a proximal section co-axially coupled proximate to a distal end of the third catheter member; and
    a separate expandable occlusion member coupled to the second catheter member near the distal end of the second catheter member and to the third catheter member near a proximal end of the third catheter member, the expandable occlusion member being positioned such that a space between the distal end of the second catheter member and the proximal end of the third catheter member is within the expandable occlusion member, wherein the distal end of the first catheter member extends into the third catheter member beyond the expandable occlusion member, and wherein the first catheter member defines a stiffness greater than a stiffness of the second catheter member and greater than a stiffness of the third catheter member, thereby defining a backbone of the catheter system, lending column strength to carry the second catheter member and the third catheter member.

2. The occlusion catheter system of claim 1, wherein the atraumatic tip member is formed of a biocompatible polymer.

3. The occlusion catheter system of claim 1, wherein the proximal section of the atraumatic tip member has a generally circular transverse cross-sectional profile and the atraumatic tip member further comprises a distal section having a generally flattened cylindrical shape.

4. The occlusion catheter system of claim 1, wherein the atraumatic tip is fabricated of a biocompatible metal.

5. The occlusion catheter system of claim 1, further comprising a pressure sensor operably associated within the first lumen and being in fluid communication with a pressure port, the pressure port positioned distally relative to the occlusion member.

6. The occlusion catheter system of claim 1, further comprising a proximal hub coupled to and in fluid flow communication with each of the first catheter member, the second catheter member and the third catheter member, the proximal hub including a first fluid pathway and a second fluid pathway, the first fluid pathway in fluid communication with the first and third lumens and the second fluid pathway in fluid communication with the second lumen.

7. The occlusion catheter system of claim 6, further comprising a fluid source coupled to the proximal hub and in fluid flow communication with the second catheter member and the occlusion member.

8. The occlusion catheter system of claim 6, further comprising a pressure sensor operably coupled to the proximal hub and in communication with the first catheter member.

9. The occlusion catheter system of claim 1, wherein a greatest outer diameter of the occlusion catheter system is less than 2.3 mm when the expandable occlusion member is not expanded.

10. The occlusion catheter system of claim 1, wherein the expandable occlusion member is a balloon.

11. The occlusion catheter system of claim 10, further comprising: a radio opaque marker fixed to the atraumatic tip member to provide a visual indication of the location of the catheter system during deployment when the radio opaque marker is irradiated.

12. The occlusion catheter system of claim 11, where the radio opaque marker is formed of a material selected from the group consisting of stainless steel, platinum iridium, a polymer mixed with a radio opaque material, barium sulfate, nitinol, a nitinol reinforced polymer and a suitable radio opaque alloy.

13. The occlusion catheter system of claim 1, wherein a first radio opaque marker is affixed near a first attachment point, the first attachment point positioned at a proximal end of the expandable occlusion member where the expandable occlusion member is connected to the second catheter member; and
    a second radio opaque marker is affixed near a second attachment point, the second attachment point positioned at a distal end of the expandable occlusion member where the expandable occlusion member is connected to the third catheter member.

14. The occlusion catheter system of claim 1, further comprising pressure sensor wires extending from the proximal section of the first catheter member to a position between the atraumatic tip member and the expandable occlusion member.

15. The occlusion catheter system of claim 1, wherein the first catheter member is constructed of a material selected from the group consisting of a metal, stainless steel, nitinol, stainless steel braiding over polyurethane, stainless steel helical windings over silicone, stainless steel helical windings over nitinol reinforced polymer, biocompatible metals and metal-reinforced polymers.

16. The occlusion catheter system of claim 1, wherein the first catheter member is constructed of nitinol.

17. The occlusion catheter system of claim 1, wherein the first catheter member is constructed of a metal-reinforced polymer.

18. The occlusion catheter system of claim 1, wherein the third catheter member includes a port passing through a side wall between the distal end and a proximal end of the third catheter member, the port being in fluid communication with the first lumen.

19. The occlusion catheter system of claim 1, wherein the third catheter member comprises a plurality of segments of distally decreasing stiffness to provide a step-down transition of stiffness toward the atraumatic tip member.

20. The occlusion catheter system of claim 1, wherein the second catheter member terminates in the annular port at the distal end of the second catheter member.

* * * * *